United States Patent [19]
Goolamali

[11] Patent Number: 5,992,428
[45] Date of Patent: Nov. 30, 1999

[54] LONG HANDLED OINTMENT APPLICATOR

[76] Inventor: Saleem Karim Goolamali, 28 Bedford Road, Middlesex, Northwood, United Kingdom, HA6 2AZ

[21] Appl. No.: 09/203,860

[22] Filed: Dec. 2, 1998

[30] Foreign Application Priority Data

Dec. 3, 1997 [GB] United Kingdom .................. 9725654

[51] Int. Cl.$^6$ ..................................................... A45D 40/26
[52] U.S. Cl. ............................ 132/320; 132/317; 401/197
[58] Field of Search ...................................... 132/320, 317, 132/207, 218, 311, 286; 401/197, 207, 208, 148, 218; 15/230.11, 118, 145, 146; 492/13

[56] References Cited

U.S. PATENT DOCUMENTS

| | | | |
|---|---|---|---|
| 3,175,241 | 3/1965 | Singleton et al. | 15/230.11 |
| 3,588,264 | 6/1971 | Mallindine | 15/230.11 |
| 3,612,707 | 10/1971 | Herbrechter | 401/197 |
| 4,387,478 | 6/1983 | Smith | 15/145 |
| 4,537,522 | 8/1985 | Charney et al. | 401/218 |
| 4,943,176 | 7/1990 | Baker | 401/197 |
| 5,176,754 | 1/1993 | Hirzel | 15/230.11 |
| 5,685,224 | 11/1997 | Dean et al. | 401/208 |
| 5,795,279 | 8/1998 | Shieh | 492/13 |
| 5,823,206 | 10/1998 | Mapleback | 132/320 |

FOREIGN PATENT DOCUMENTS

| | | |
|---|---|---|
| 2 046 596 | 11/1980 | United Kingdom . |
| 2 160 105 | 12/1985 | United Kingdom . |
| 2 263 508 | 7/1993 | United Kingdom . |

*Primary Examiner*—Gene Mancene
*Assistant Examiner*—Pedro Philogene
*Attorney, Agent, or Firm*—Larson & Taylor

[57] ABSTRACT

A long handled ointment applicator comprises a non-absorbent roller rotatably carried by an elongate handle member at one end thereof, and on the applicator for enabling a user to measure out a predetermined dose of ointment for application to the surface of the roller. An arm is pivotally mounted on the handle member so that it is movable between a first position in line with the handle member and a second position in which an arcuate recess in the arm is applied to the surface of the roller, and the measuring means is constituted by a depression having a predetermined volume formed in the arm within the arcuate recess.

11 Claims, 1 Drawing Sheet

LONG HANDLED OINTMENT APPLICATOR

BACKGROUND OF THE INVENTION

The invention relates to an ointment applicator particularly, but not exclusively, intended for the application of medicated ointment to parts of the body that are difficult or impossible to reach by one's own hand. For example, even a reasonably agile person has difficulty reaching all parts of his or her back, and arthritic and aged persons generally find it impossible to reach much of the back and often also the feet and lower parts of the legs. In these circumstances it is necessary either for someone else to apply the ointment to those parts which the person cannot reach, or for the person to use a long handled applicator to apply the ointment to the hard to reach places.

Various examples of such an applicator comprising a non-absorbent roller rotatably carried by and readily removable (for cleaning purposes) from an elongate carrier member at or near one end thereof are disclosed in GB-A-2046596. A person wishing to use the applicator to apply ointment (or any other preparation) topically to a part of the body which is out of normal reach simply spreads the ointment on the surface of the roller and then, holding the applicator by the handle end of the carrier member, guides the applicator so that the roller is caused to roll back and forth over the area of the body to which the ointment is to be applied.

One problem which many people have when applying ointment, whether using an applicator or not, is determining exactly how much should be applied. For example, the recommended dose for a single application to a particular area may be 1 gram, but when dispensing ointment from a tube it is difficult to gauge such an amount accurately. Accordingly, it is often the case that too much ointment is applied, which is wasteful, or too little, which may reduce the efficacy of the treatment.

SUMMARY OF THE INVENTION

The invention aims to overcome this problem, at least for users of a long handled ointment applicator, by providing such an applicator comprising a non-absorbent roller rotatably carried by an elongate handle member at or near one end thereof, and a measuring device having measuring means for enabling a user to measure out a predetermined dose of ointment, the measuring device comprising an arm which is pivotally mounted on the handle member so that it is movable between a first position in which the measuring means is used to measure out the predetermined dose of ointment, and a second position in which the measuring means is applied to the surface of the roller to transfer the ointment to the roller.

Preferably the measuring means comprises a depression for receiving ointment dispensed by the user, the depression having a predetermined volume such that it defines a measured dose when filled with the ointment. For example, the volume may be designed to define a 1 gram dose of ointment (assuming that most ointments have much the same density as each other), although different volumes defining different doses can of course be used.

In some circumstances, however, it may be necessary for the user to use a finger to spread the transferred ointment more evenly over the surface of the roller and possibly also to ensure that all of the ointment is transferred from the measuring means to the roller.

In one embodiment, the measuring means is provided in an arcuate recess in the arm, the recess having a radius of curvature corresponding to that of the roller surface and being positioned in the arm such that it fits closely around a portion of the roller surface when the arm is in the second position.

The arm may be pivotally mounted in an aperture in the handle member and be arranged to lie in the aperture substantially in line with the handle member in the first position of the arm, the arm preferably having a stop which engages a portion of the handle member to prevent the arm from pivoting beyond the first position when it is returned from the second position.

As in the applicators described in GB-A-2046596, the roller is preferably readily detachable from the handle member to facilitate cleaning of the applicator. In a preferred arrangement, the roller end of the handle member defines a fork having two spaced prongs and the roller is rotatably mounted between the two prongs, the roller preferably being a snap-fit into position between the prongs.

The roller may be made of any suitable non-absorbent material, such as metal or plastics, and is preferably formed as a unitary member. For example, the roller may be cast from aluminium or a light weight alloy, but preferably it is integrally moulded from a suitable plastics material. The outer diameter of the roller may be between 2 and 10 cm, but is preferably between 3 and 8 cm and more preferably between 3 and 6 cm. Its width (i.e. in the direction of its axis of rotation) may be between 2 and 9 cm, and is preferably between 2 and 7.5 cm and more preferably between 2.5 and 6 cm. The profile of the roller surface across its width will usually be straight, but may be made slightly convex if preferred.

Similarly, the handle member may also be made of any suitable material such as plastics, metal or even wood, but preferably it is of moulded plastics construction. It may be formed integrally as a unitary member, or in two or more parts which are either detachably or permanently fixed together. The handle member will preferably be straight, but may be slightly curved or bent if necessary to facilitate access to some parts of the body. Generally, the handle member will be arranged to carry the roller so that the roller axis is at right angles to the longitudinal axis of the handle member. As an alternative, however, the applicator may be arranged so that the roller axis is substantially parallel to the longitudinal axis of the handle member. The overall length of the handle member will generally be between 15 and 50 cm, but is preferably between 30 and 48 cm and more preferably between 32 and 42 cm.

One embodiment of a long handled ointment applicator in accordance with the invention will now be described, by way of example, with reference to the accompanying drawings.

DESCRIPTION OF THE PREFERRED EMBODIMENT

The drawings show a long handled ointment applicator 1 comprising an elongate handle member 2 and a roller 3 rotatably mounted in a detachable manner at one end of the member 2.

Figure 4:
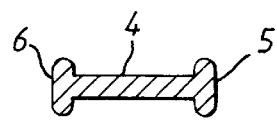

The handle member 2 is an elongate unitary moulded plastics member having a central flat web portion 4 bounded by strengthening flanges 5, 6 along the longitudinal side edges of the web 4 to provide the member with a substantially I-shaped cross section in a plane perpendicular to the longitudinal axis of the member as shown in FIG. 4. At the end of the handle member 2 remote from the roller 3, the side flanges 5, 6 are joined in a continuous manner around a radiused end portion of the central web 4 to provide the handle member 2 with a smoothly curved end 7. The web 4 may be provided with an eye 8 near the end 7 so that the applicator can be hung on a hook when not in use.

The width of the handle member 2 is substantially uniform between the curved handle end 7 and a point approximately mid-way along its length, and reduces gradually from the mid-point to a position near the roller end of the member 2 where the side flanges 5, 6 turn outwards away from each other to form shoulders 5a, 6a and then turn parallel to the longitudinal axis of the member 2 to form two parallel prongs 5b, 6b extending beyond the web portion 4 to define a forked end 9 for receiving the roller 3. The height and thickness of the prongs 5b, 6b are slightly greater than the height and thickness of the side flanges 5, 6, and each prong is formed with a similar U-shaped slot 10 which opens centrally in the free end of the prong. The root of each slot 10 defines an arcuate socket 11 which subtends an angle greater than 180° at its centre of curvature and which has a diameter very slightly greater than the distance between the walls of the slot 10 leading into the socket 11.

The roller 3 which is also formed as a unitary plastics moulding, comprises a cylindrical outer portion 12 which has a smooth, non-absorbent outer surface 13 and an axial length which is slightly less than the distance between the prongs 5b, 6b. The cylindrical portion 12 coaxially surrounds an inner hub 14 of the roller and is rigidly joined to the hub by an annular web 15 disposed perpendicularly to the roller axis and mid-way between the ends of the hub and the cylindrical portion. The hub is formed with a reduced diameter portion at each end forming a pair of similar stub axles 16 which project beyond the end planes of the cylindrical portion 12 for the purpose of rotatably mounting the roller 3 in the forked end 9 of the handle member 2. The diameter of the stub axles 16 is such that they can be pushed into the slots 10 in the free ends of the prongs 5b, 6b until they snap into the sockets 11 where they are held captive to retain and mount the roller in a freely rotatably manner on the handle member. This arrangement allows the roller 3 to be readily detached and re-fitted as desired.

Figure 1:
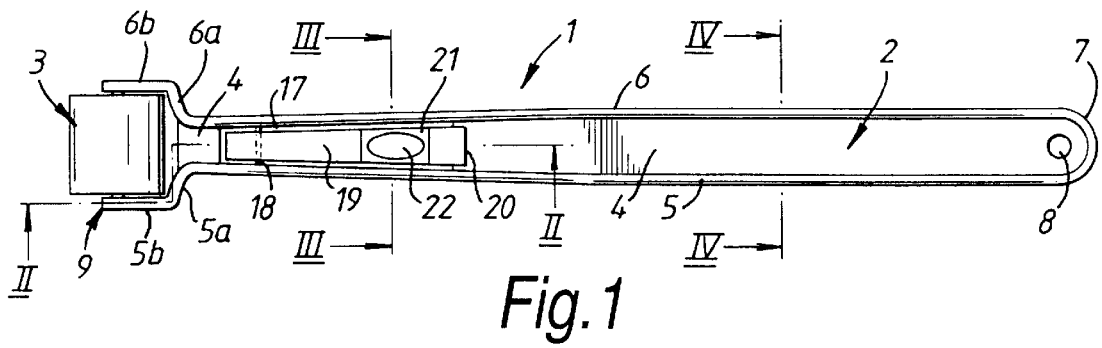
FIG. 1 shows a plan view of the applicator.
Figure 2:
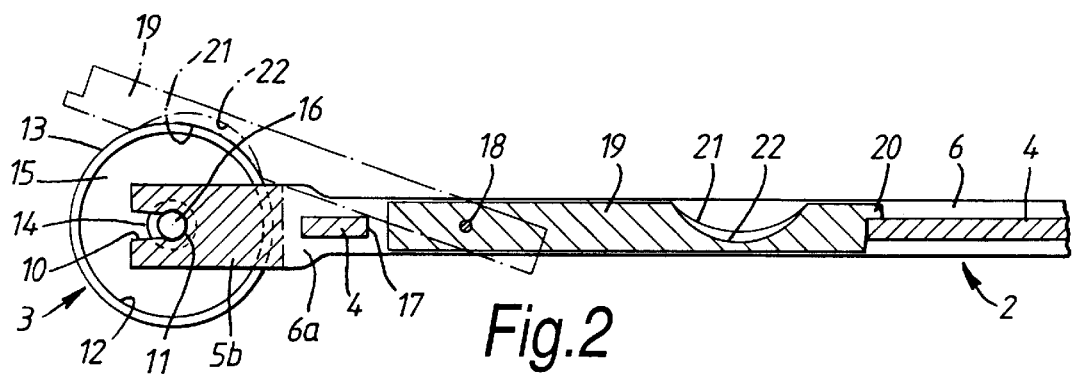
FIG. 2 shows a longitudinal section through a portion of the applicator taken on line 2—2 of FIG. 1.
Figure 3:
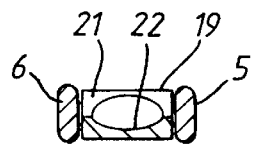
FIG. 3 is a transverse section through the applicator taken on the line 3—3 of FIG. 1; and, FIG. 4 is a transverse section through the applicator taken on the line 4—4 of FIG. 1.

Near the roller end of the handle member 2 the web portion 4 is provided with an elongate aperture 17, and a pivot pin 18 is mounted across the aperture near the roller end thereof, the ends of the pivot pin being supported by the flanges 5, 6 on opposite sides of the aperture. A lever 19 forming an ointment measuring and transfer device is pivotally mounted on the pin 18 so that it is pivotable between a first position (shown in full lines in FIG. 2) in which it is received in the aperture 17 and lies substantially within the confines of the handle member as defined by the upper and lower edges of the flanges 5, 6, and a second position (as shown in chain lines in FIG. 2) in which the lever lies across the outer surface 13 of the roller 3 in a substantially tangential direction. The lever 19 has a stop 20 at its end furthest from the pivot pin 18 for engaging the web 4 adjacent the handle end of the aperture 17 to define the first position. The lever 19 further has an arcuate recess 21 which has a radius of curvature corresponding to that of the roller surface 13 and which is positioned so that in the second position a portion of the roller surface 13 is received in and engaged by the arcuate recess 21 of the lever. Within the arcuate recess 21 the surface of the lever is provided with a depression 22 having a predetermined volume such that it will hold a specific amount of ointment when it is filled with ointment to the level of the surface of the recess surrounding the depression 22. Usually the volume of the depression 22 will be designed to hold approximately 1 gram of ointment, which is a commonly used dose for many treatments, but other volumes may be used.

In use, therefore, ointment is deposited in the depression 22 when the lever 19 is in its first position (or perhaps slightly raised therefrom if this is more convenient) and then smoothed to the level of the surface of the arcuate recess 21 around the depression in order to ensure that the depression contains the desired measured dose. The lever 19 is then pivoted to its second position over the roller 3 so that the ointment is deposited from the depression 22 onto the surface 13 of the roller. Rotation of the roller will tend to draw the ointment from the depression 22, but in order to ensure that all of the ointment is transferred to the roller it may be necessary to lift the lever from the roller surface so that the user can remove any remaining ointment from the depression using his or her finger. To facilitate this (and also subsequent cleaning of the lever) the surface within the depression 22 is preferably curved and smooth. The lever is then returned to its rest position, and the applicator used to apply the roller to the desired area and to move the roller back and forth over the area and thereby apply the ointment evenly to the area.

I claim:

1. A long handled ointment applicator comprising an elongate handle member, a non-absorbent roller rotatably carried by said elongate handle member near one end thereof, and a measuring device having measuring means for enabling a user to measure out a predetermined dose of ointment, the measuring device comprising an arm which is pivotally mounted on the handle member so that it is movable between a first position in which the measuring means is used to measure out the predetermined dose of ointment, and a second position in which the measuring means is applied to the surface of the roller to transfer the ointment to the roller.

2. An applicator according to claim 1, wherein said measuring means comprises a depression for receiving ointment dispensed by the user, the depression having a predetermined volume such that it defines a measured dose when filled with the ointment.

3. An applicator according to claim 1 or claim 2, wherein said measuring means is provided in an arcuate recess in the arm, the recess having a radius of curvature corresponding to that of the roller surface and being positioned in the arm such that it fits closely around a portion of the roller surface when the arm is in the second position.

4. An applicator according to claim 3, wherein said arm is pivotally mounted in an aperture in the handle member and lies in the aperture substantially in line with the handle member in the first position of the arm.

5. An applicator according to claim 4, wherein said arm has a stop which engages a portion of the handle member to prevent the arm from pivoting beyond the first position when it is returned from the second position.

6. An applicator according to claim 1, wherein said roller is detachable from the handle member.

7. An applicator according to claim 1, wherein the roller end of the handle member defines a fork having two spaced prongs, and the roller is rotatably mounted between the two prongs.

8. An applicator according to claim 7, wherein said roller is a snap-fit into position between the two prongs.

9. An applicator according to claim 1, wherein the length of the handle member is between 15 cm and 50 cm, and is preferably between 32 and 42 cm.

10. An applicator according to claim 1, wherein the diameter of the roller is between 2 cm and 10 cm, and is preferably between 3 and 6 cm.

11. An applicator according to claim 1, wherein the width of the roller (in the direction of its axis of rotation) is between 2 cm and 9 cm, and is preferably between 2.5 and 6 cm.

* * * * *